(12) United States Patent
John

(10) Patent No.: US 11,520,170 B2
(45) Date of Patent: Dec. 6, 2022

(54) EYEWEAR MOUNTING DEVICE

(71) Applicant: Alexander John, Norwich, CT (US)

(72) Inventor: Alexander John, Norwich, CT (US)

(73) Assignee: Alexander John, Norwich, CT (US)

( * ) Notice: Subject to any disclaimer, the term of this patent is extended or adjusted under 35 U.S.C. 154(b) by 329 days.

(21) Appl. No.: 16/737,069

(22) Filed: Jan. 8, 2020

(65) Prior Publication Data
US 2020/0218091 A1 Jul. 9, 2020

Related U.S. Application Data

(60) Provisional application No. 62/789,806, filed on Jan. 8, 2019.

(51) Int. Cl.
| | | |
|---|---|---|
| *G02C 11/04* | (2006.01) | |
| *G02C 11/00* | (2006.01) | |
| *A45F 5/02* | (2006.01) | |

(52) U.S. Cl.
CPC .......... *G02C 11/10* (2013.01); *A45F 5/02* (2013.01); *G02C 11/04* (2013.01); *A45F 2200/05* (2013.01)

(58) Field of Classification Search
CPC ........ G02C 11/00; G02C 3/003; G02C 3/006; Y10T 24/1498
See application file for complete search history.

(56) References Cited

U.S. PATENT DOCUMENTS

| | | | | | |
|---|---|---|---|---|---|
| 3,856,007 | A | * | 12/1974 | Leight | .............. G02C 11/00 128/866 |
| 5,475,449 | A | * | 12/1995 | Pyle | .............. A61F 11/12 181/130 |
| 5,598,994 | A | * | 2/1997 | Olewinski | .......... F16B 37/0842 248/73 |
| 5,703,670 | A | * | 12/1997 | Callard | .............. A61F 11/12 351/123 |
| 5,722,762 | A | * | 3/1998 | Soll | .............. F21L 15/14 362/105 |
| 5,781,272 | A | * | 7/1998 | Bright | .............. A61F 9/029 351/123 |
| 5,926,921 | A | * | 7/1999 | Benoit | .............. B65D 63/1081 24/16 PB |
| 6,073,315 | A | * | 6/2000 | Rasmussen | .......... B65D 63/1018 24/16 PB |
| 6,082,855 | A | * | 7/2000 | Fleming | .............. A61F 9/029 351/123 |
| 6,183,178 | B1 | * | 2/2001 | Bateman | .............. B60P 7/0807 410/106 |

(Continued)

FOREIGN PATENT DOCUMENTS

CN 205198563 U * 5/2016
WO WO-2012084203 A1 * 6/2012 ............ G02C 3/003

*Primary Examiner* — Christopher Stanford
(74) *Attorney, Agent, or Firm* — Wiggin and Dana LLP

(57) ABSTRACT

A hardware mounting system for eyewear including a mounting bracket that is secured to a temple of eyewear by wrapping a stretchable retention band around the temple and aligning two openings in the retention band around a protrusion in the mounting bracket. Either or both of a mounting arm and a spherical rod end can be secured to the mounting bracket. The mounting arm can allow an ear device such as hearing protection to be secured to the eyewear. The spherical rod end allows a device having a socket such as certain illumination devices to be secured to the eyewear.

10 Claims, 27 Drawing Sheets

(56) References Cited

U.S. PATENT DOCUMENTS

| | | | | |
|---|---|---|---|---|
| 6,634,063 B2* | 10/2003 | Joseph | ............ | F16L 3/233 |
| | | | | 174/135 |
| 7,641,334 B1* | 1/2010 | Goldie | ............ | A61F 11/12 |
| | | | | 351/123 |
| 7,997,721 B1* | 8/2011 | Burcham | ............ | G02C 5/20 |
| | | | | 351/123 |
| 8,820,921 B1* | 9/2014 | Lier | ............ | G02C 5/143 |
| | | | | 351/123 |
| 9,309,033 B2* | 4/2016 | Dorsey | ............ | H02G 3/32 |
| 10,070,673 B2* | 9/2018 | Mendez | ............ | G02C 11/12 |
| 10,323,774 B2* | 6/2019 | Van Hulst | ............ | F16B 37/0857 |
| 11,209,666 B2* | 12/2021 | Necklas | ............ | G02C 3/006 |
| 2003/0160939 A1* | 8/2003 | Webber | ............ | G02C 3/003 |
| | | | | 351/114 |
| 2011/0255049 A1* | 10/2011 | Corona | ............ | G02C 11/00 |
| | | | | 351/123 |
| 2016/0258455 A1* | 9/2016 | Chang | ............ | G02C 3/006 |
| 2020/0124873 A1* | 4/2020 | Jones | ............ | A61F 9/027 |
| 2020/0218094 A1* | 7/2020 | Howell | ............ | G02C 11/06 |
| 2020/0400969 A1* | 12/2020 | Fedorov | ............ | G02C 5/122 |

* cited by examiner

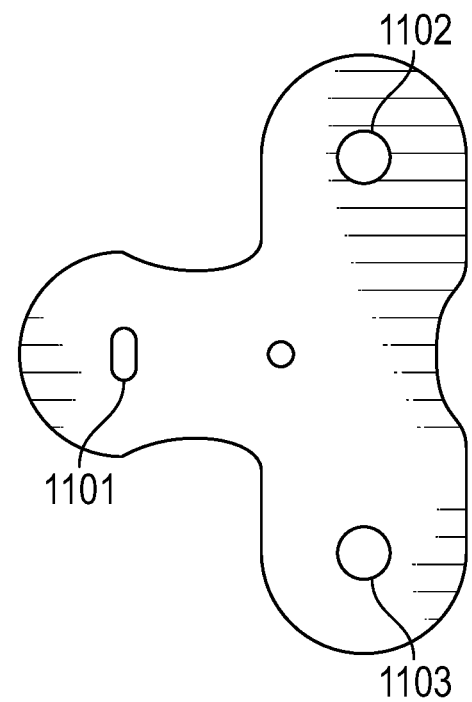
FIG. 11A
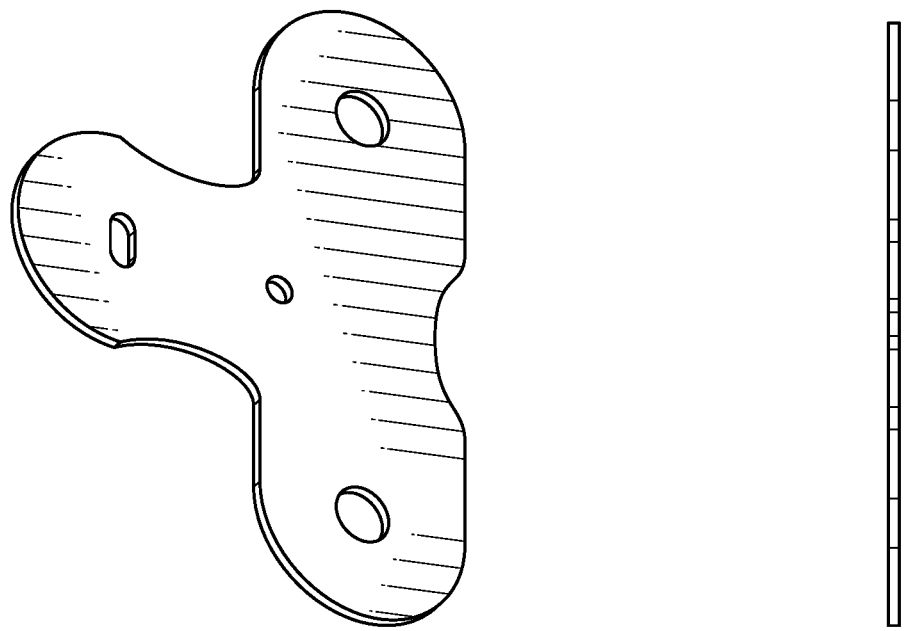
FIG. 11B
FIG. 11C

EYEWEAR MOUNTING DEVICE

RELATED APPLICATION

This application claims the benefit of U.S. Provisional Patent Application No. 62/789,806 filed Jan. 8, 2019 and entitled "Eyewear Mounting Device." The entire contents of U.S. 62/789,806 are hereby incorporated herein in their entirety.

FIELD OF INVENTION

The present disclosure relates to mounting hardware to eyewear and more particularly relates to a mounting solution adaptable to a variety of eyewear.

BACKGROUND

It can be desirable to selectively employ certain devices such as hearing protection or illumination tools at the same time as eyewear. However, it is easy to lose such devices or have them become dirty when repeatedly switching out their use. It is desirable to have a solution for securing such devices in the vicinity of earwear without requiring custom eyewear.

SUMMARY

Disclosed is a mounting system for securing devices such as hearing protection, electronic ear buds, illumination tools etc. to eyewear in a removable manner so a user can switch between using the devices and have them disposed in the vicinity of the eyewear so that they do not need to be separately stored.

A mounting bracket is disposed against a temple of eyewear and a stretchable retention band is wrapped around the temple until tight, with two openings in the retention band being aligned around a portion of the mounting bracket. In this manner the mounting bracket can be removed if no longer desired. Further, the employment of a stretchable retention band with a series of openings allows for the adaptation of the mounting bracket to eyewear of varying sizes/geometries.

If earwear is desired to be attached, a mounting arm is secured to the mounting bracket, which extends from the mounting bracket backwards (relative to the user's face) to the vicinity of the user's ear when the eyewear is donned. The mounting arm preferably has a slot profile in it which allows adjustment of the distance between the mounting bracket and the user's ears to accommodate various head and eyewear geometries. Various adapters allow securement of ear devices such as electronic earbuds to the mounting arm. When not in use, the mounting arm can be rotated up or downwards to dispose the earwear away from the user's ears but easily reachable.

If an illumination device is desired, a spherical end rod can be secured to the mounting bracket and a socket of the illumination device can be secured to the spherical end.

BRIEF DESCRIPTION OF THE DRAWINGS

FIGS. 11A-C depict detailed views of the second adapter of the second embodiment.

DETAILED DESCRIPTION

Disclosed is a mounting system for augmenting eyewear, such as glasses, sunglasses, and safety glasses, with additional hardware. Such hardware can include hearing protection, electronic hearing buds, an illumination device, and/or ear warmers, etc.

Figure 1A:
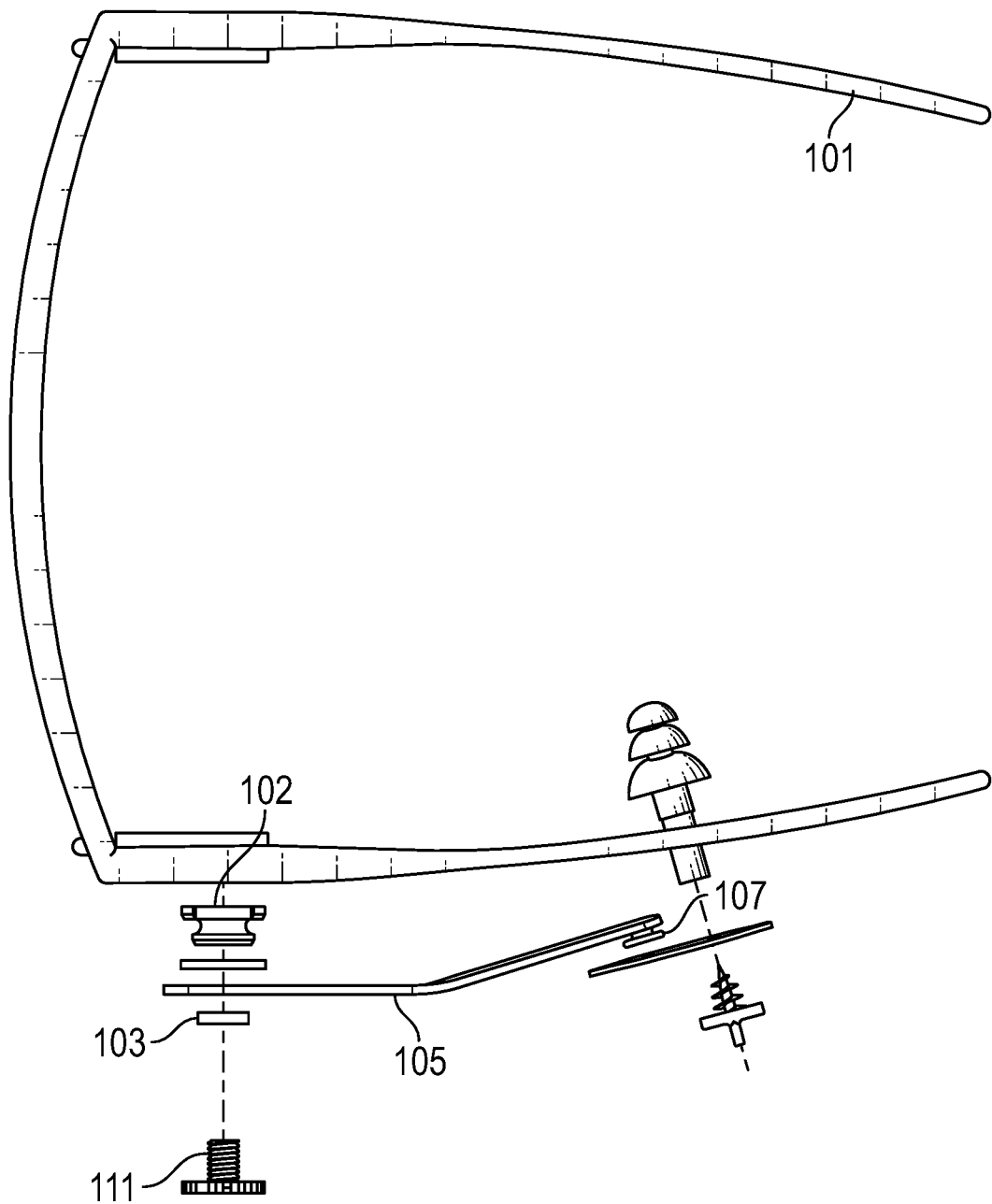
FIGS. 1A-C depict various views of a blow-up diagram of an embodiment mounting system.
Figure 1B:
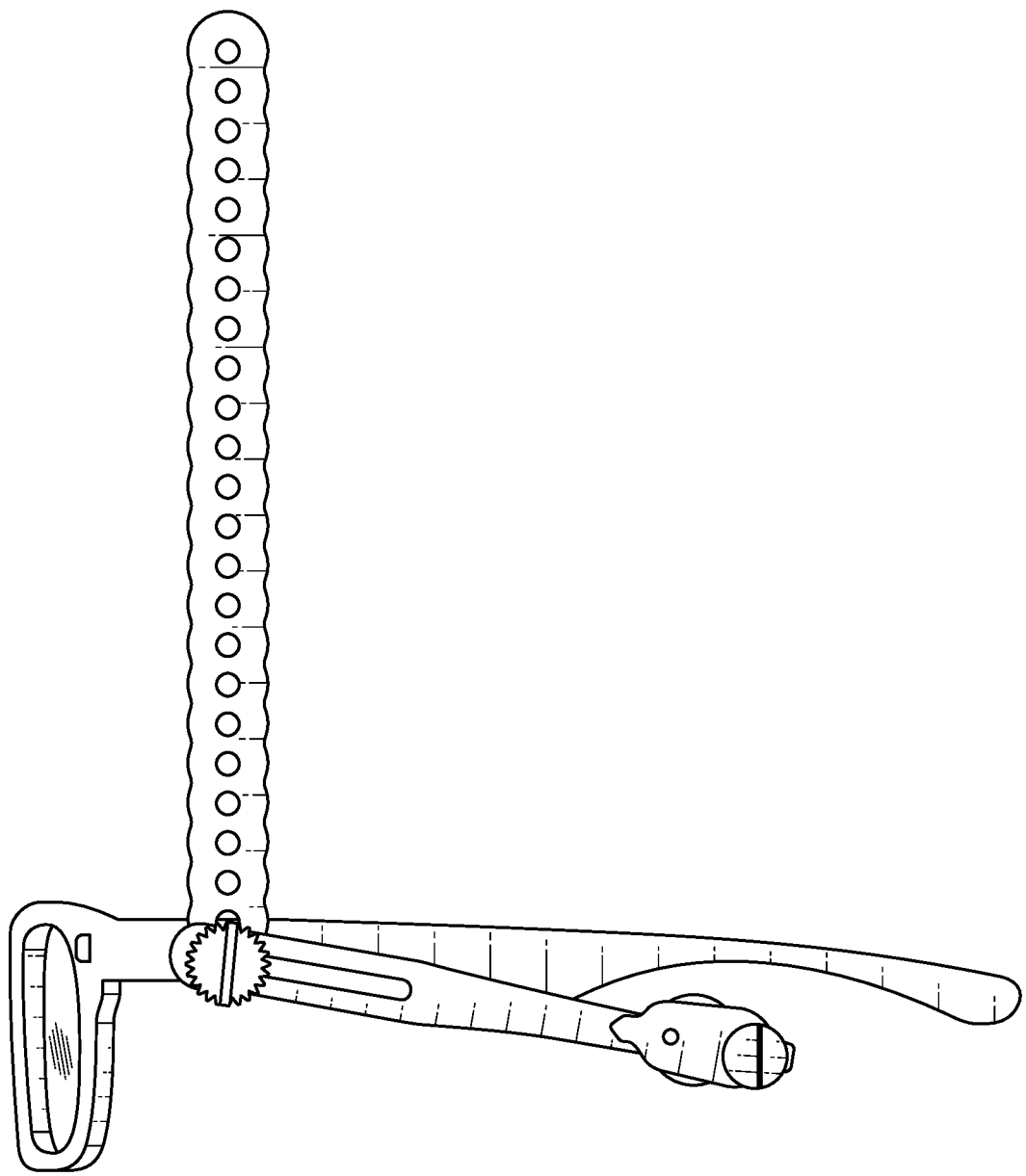
Figure 1C:
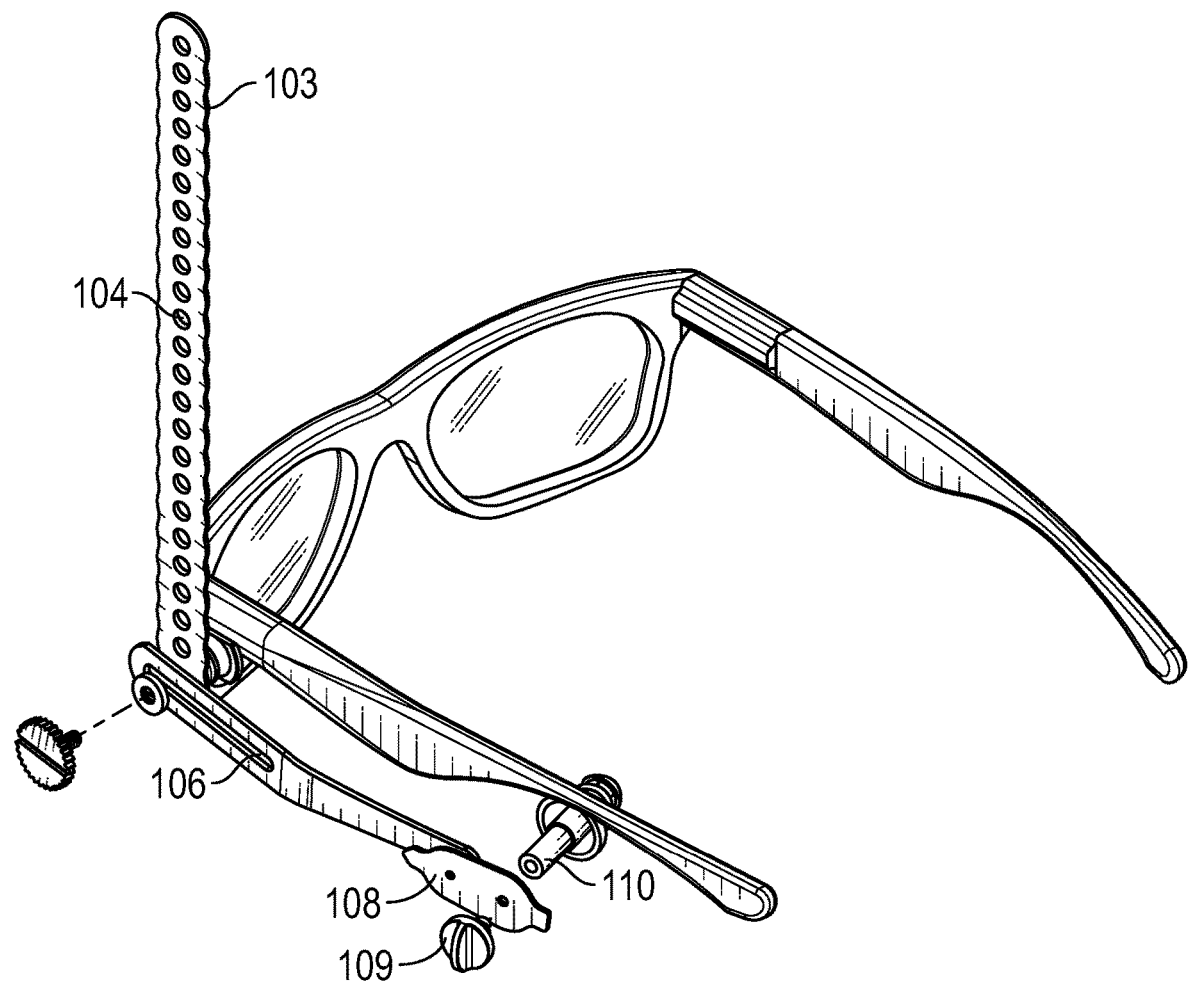

With reference to FIG. 1, attachment is made to eyewear 101. A mounting bracket 102 has a central section having a circumferential indentation, a mounting section and a retention section. During installation the mounting section is placed against a forward temple of eyewear 101. An elastic retention band 103 having a plurality of adjustment openings 104 is wrapped around the temple of the eyewear until two adjustment openings overlap and are secured on the retention section of the mounting bracket 102. The elastic retention band 103 has sufficient elasticity to allow it to be compressively wrapped around the temple and have the adjustment openings 104 fit around the retention section of the mounting bracket when the adjustment openings 104 are of a smaller diameter than the largest diameter of the retention section of the mounting bracket 102. Preferably, the retention band 103 has a gripping surface to aid in securement.

Next, a mounting arm 105 may be installed. The mounting arm has a slot profile 106 and a retention section 107. The slot profile allows the mounting arm to be secured at an adjustable position relative to the temple, thus allowing the positioning of an ear attachment to be adjusted. Preferably, the mounting arm has a bend to position the ear attachment adjacent to the user's ear when in a deployed position.

Figure 15:
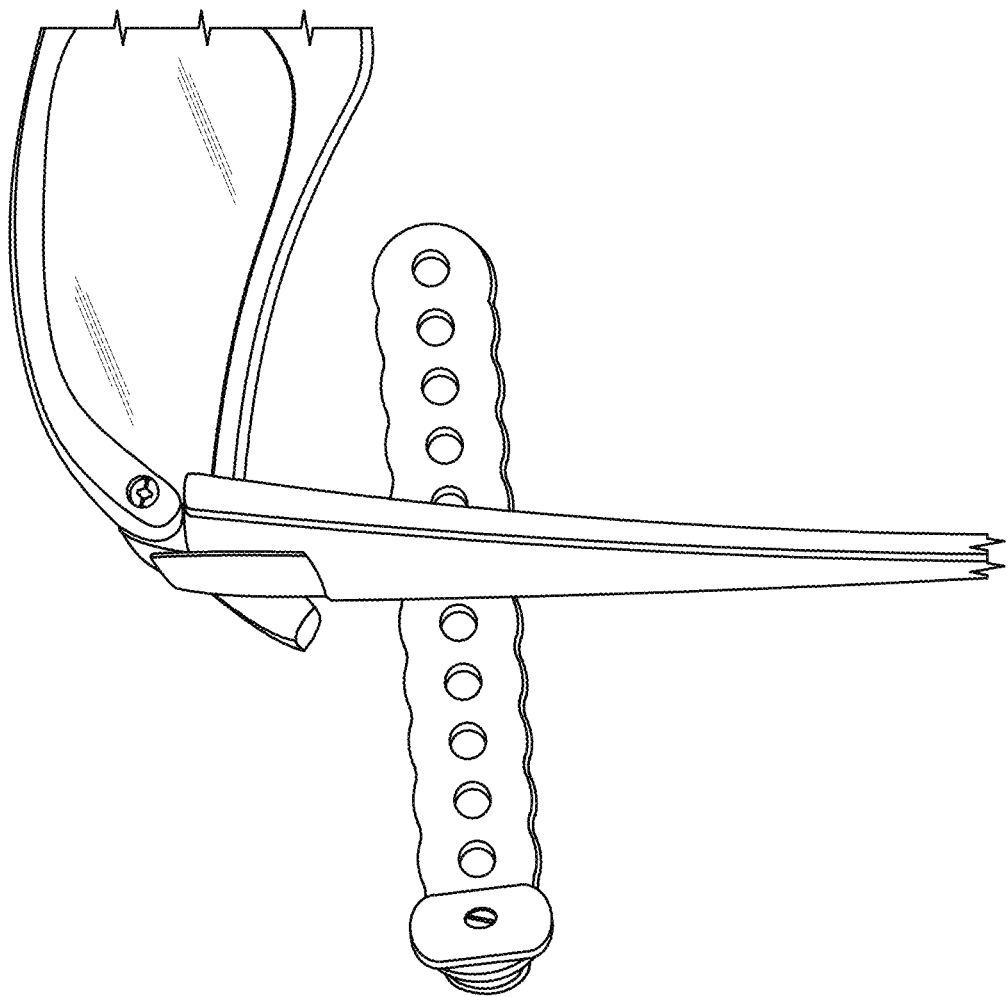
FIG. 15 depicts a retention band with a number of openings configured to be wrapped around a temple of the eyewear.
Figure 16:
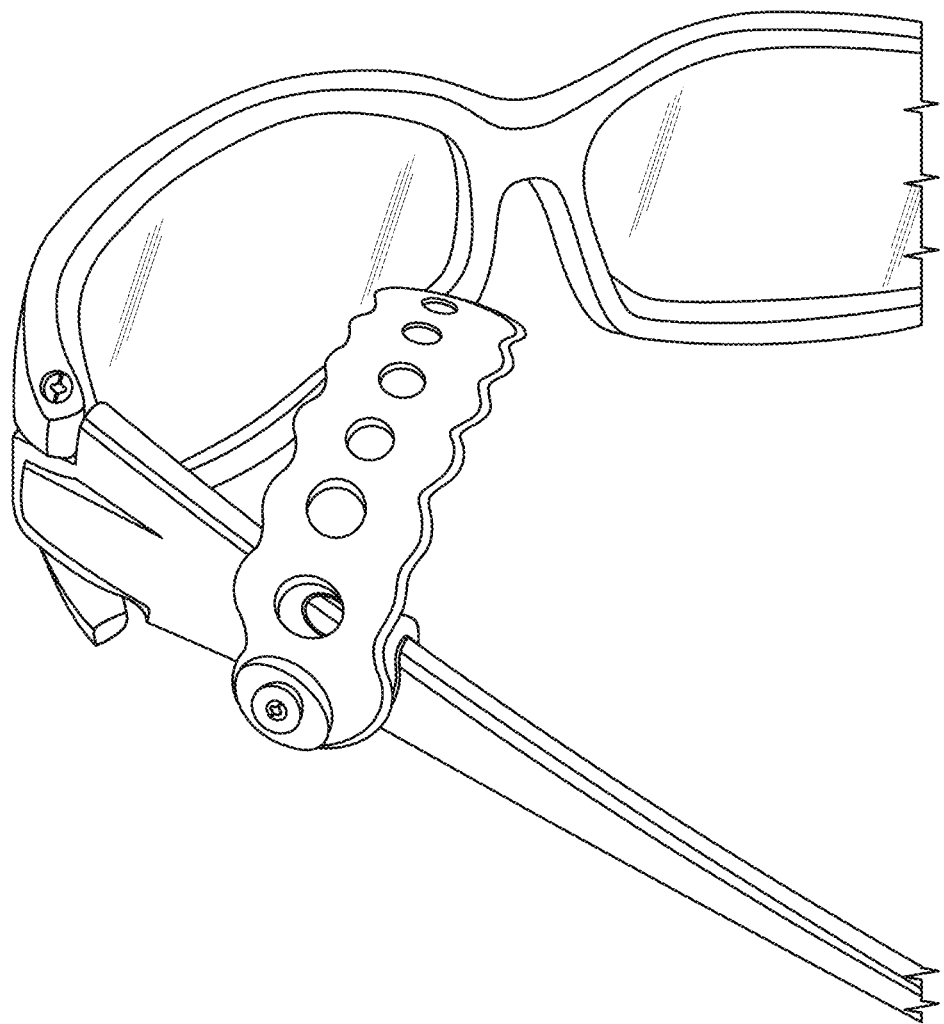
FIG. 16 depicts a retention band with a number of openings which is wrapped around a temple of the eyewear.
Figure 17:
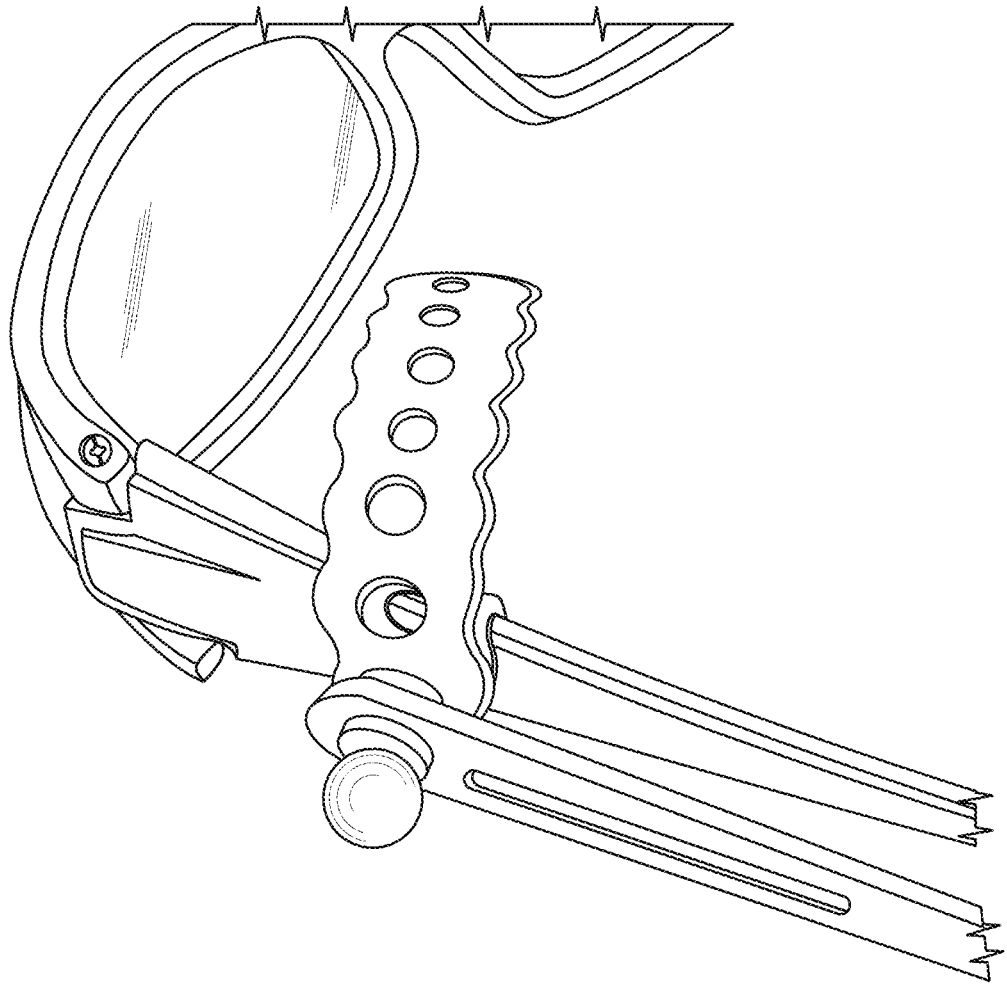
FIG. 17 depicts a mounting arm mounted to a temple of the eyewear in conjunction with the retention band.
Figure 18:
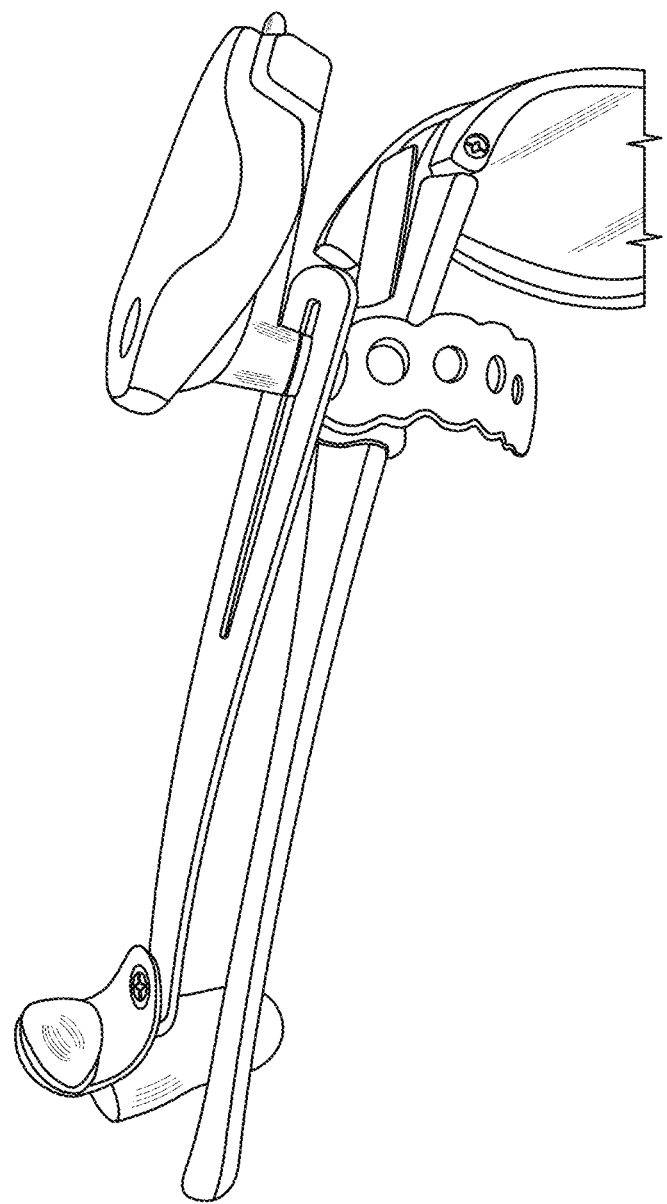
FIG. 18 further depicts a mounting arm mounted to a temple of the eyewear in conjunction with the retention band.

Referring now to FIG. 15, therein is depicted a retention band with a number of openings configured to be wrapped around a temple of the eyewear. Referring now to FIG. 16, therein is depicted a retention band with a number of openings which is wrapped around a temple of the eyewear. Referring now to FIG. 17, therein is depicted a mounting arm mounted to a temple of the eyewear in conjunction with the retention band. Referring now to FIG. 18, therein is depicted a mounting arm mounted to a temple of the eyewear in conjunction with the retention band.

During installation, the slot profile 106 of the mounting arm is positioned against the retention section of the mounting bracket. Preferably, an o-ring or bracket is placed between the retention section of the mounting bracket and the mounting arm. Next, a thumbscrew 111 is placed through the mounting arm and secured into an internal cavity of the mounting bracket. In the depicted embodiment, the thumbscrew 111 has a flat head, but as is discussed below, a spherical rod end may be employed.

Preferably, an o-ring or bracket is placed between the mounting arm and the thumbscrew. The o-rings provide rotational resistance so that the positioning of the mounting arm can be adjusted.

Adapters may be secured to the retention section 107 of the mounting arm. For example, in FIG. 1, a first opening of hearing protection adapter 108 is secured to the retention section of the mounting bracket. In the embodiment, a self-tapping thumbscrew 109 is inserted through a second opening of adapter 109 and secured into a soft hearing protection bud 110.

Figure 2:
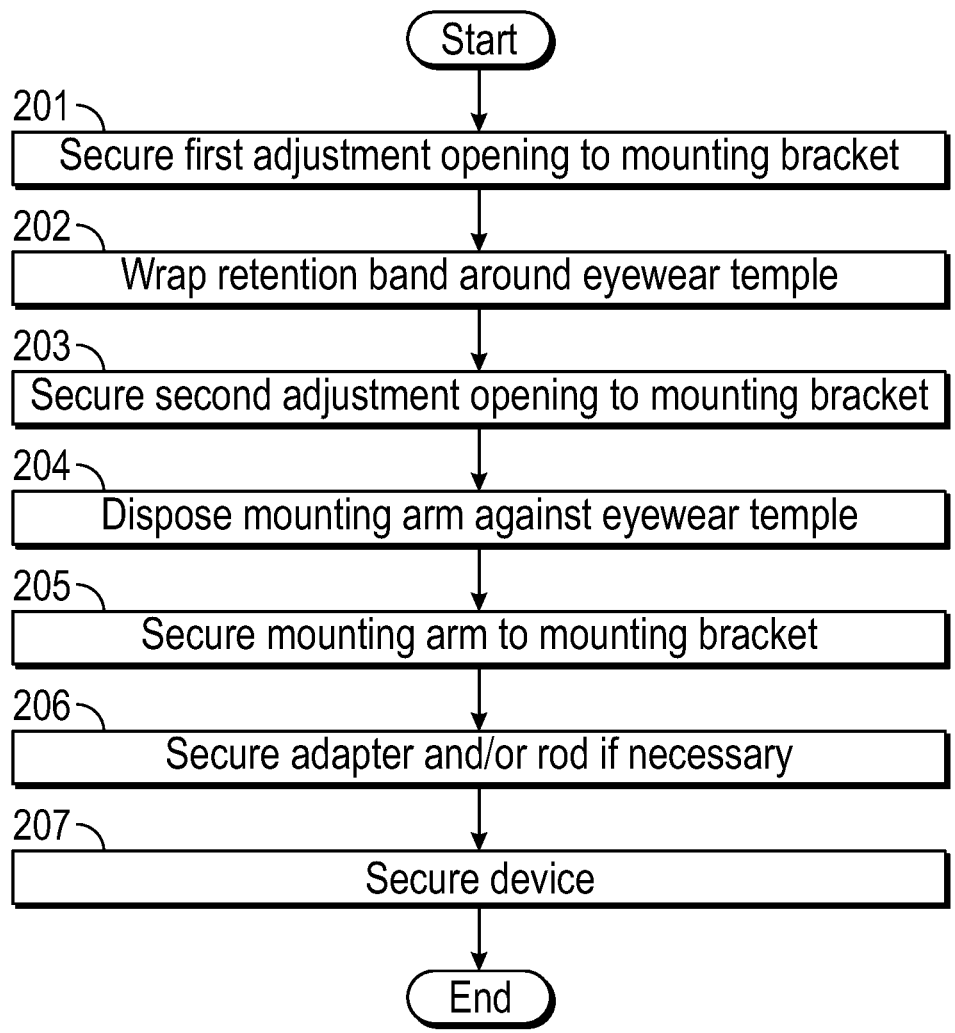
FIG. 2 depicts a flowchart of an embodiment mounting system method.
Figure 3A:
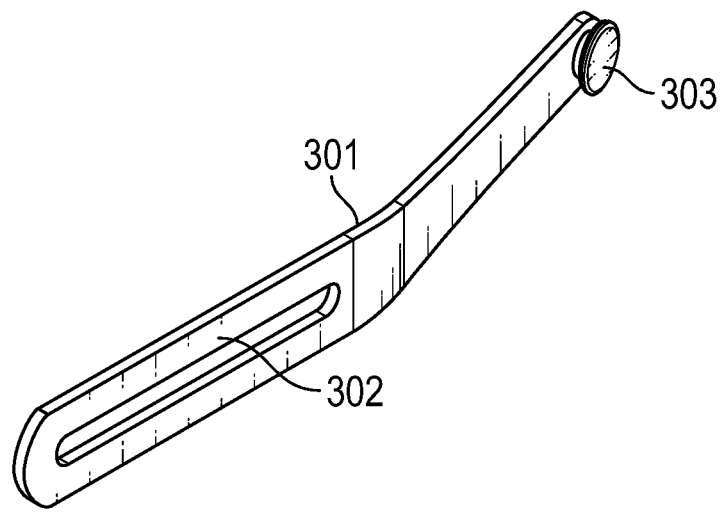
FIGS. 3A-E depict detailed views of a mounting arm of an embodiment.
Figure 3B:
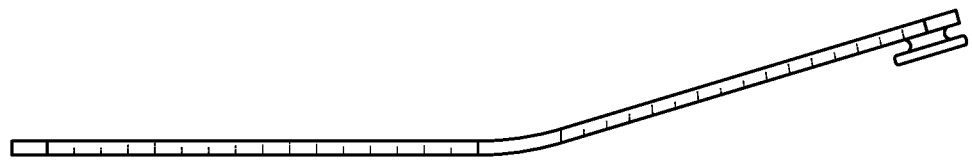
Figure 3C:
Figure 3D:
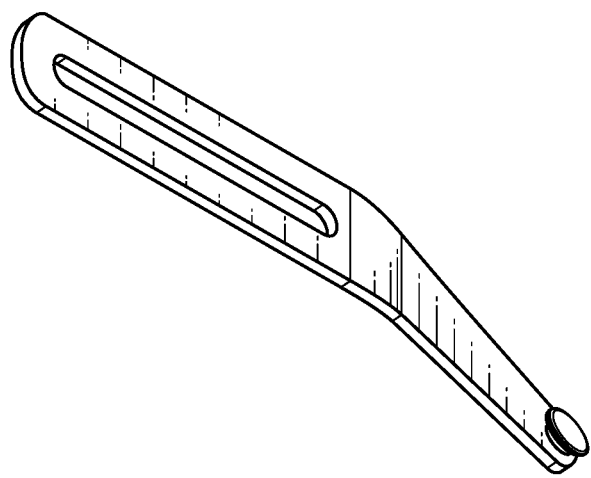
Figure 3E:
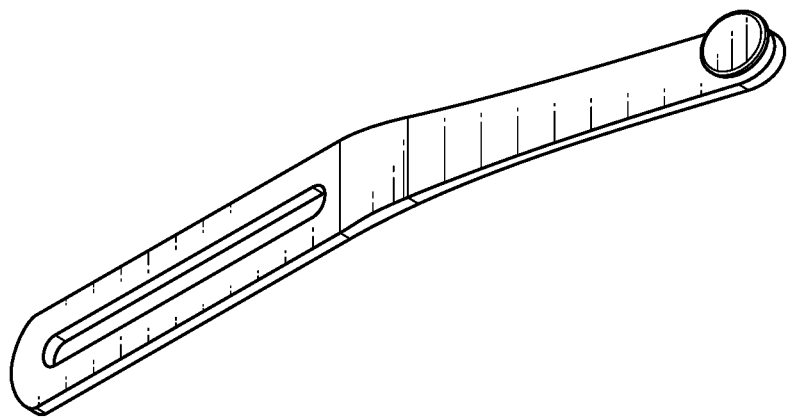

FIG. 2 is a flowchart detailing an embodiment method. In step 201, the last adjustment opening in the retention band is secured to the mounting bracket. In step 202, the retention band is wrapped around the eyewear temple, and stretched slightly to align a second adjustment opening in the retention band with the axis of a threaded depression in the mounting bracket and secured around the circumferential indentation in the mounting bracket. Preferably the mounting bracket has a circumferential lip to help retain the retention band. The retention band may then be selectively trimmed to eliminate excess adjustment openings. Depending on the geometry of the temple of the eyewear, varying numbers of adjustment openings may be employed. In step 204, a mounting arm is placed against the mounting bracket. Next, in step 205, the mounting arm is secured to the mounting bracket. This may be accomplished using a thumbscrew with a flat surface or a thumbscrew with a spherical rod end. In step 206, an adapter is secured to the mounting arm. The adapter type may depend on the type of device to be secured. For instance a flat plate adapter with two openings may have one opening secured to the mounting bracket and a second opening secured to soft hearing protection through the use of a thumbscrew in step 207. In certain other embodiments, a T-shaped adapter may have two openings configured to receive the stem of an earbud type headphone.

FIGS. 3A-E depict detailed views of a mounting arm 301 of an embodiment. The mounting arm 301 has a slot profile through which attachment devices may be used to secure the mounting arm 301 to a mounting bracket. The mounting arm 301 may have an angled geometry to position devices close to a user's ear. The mounting arm includes an attachment point 303 which may include a protruding tab, threaded orifice or other geometry configured to interface with an adapter or directly with an ear device. In certain instances, the mounting arm may be collapsible or telescoping.

Figures 4A, 4B, 4C:
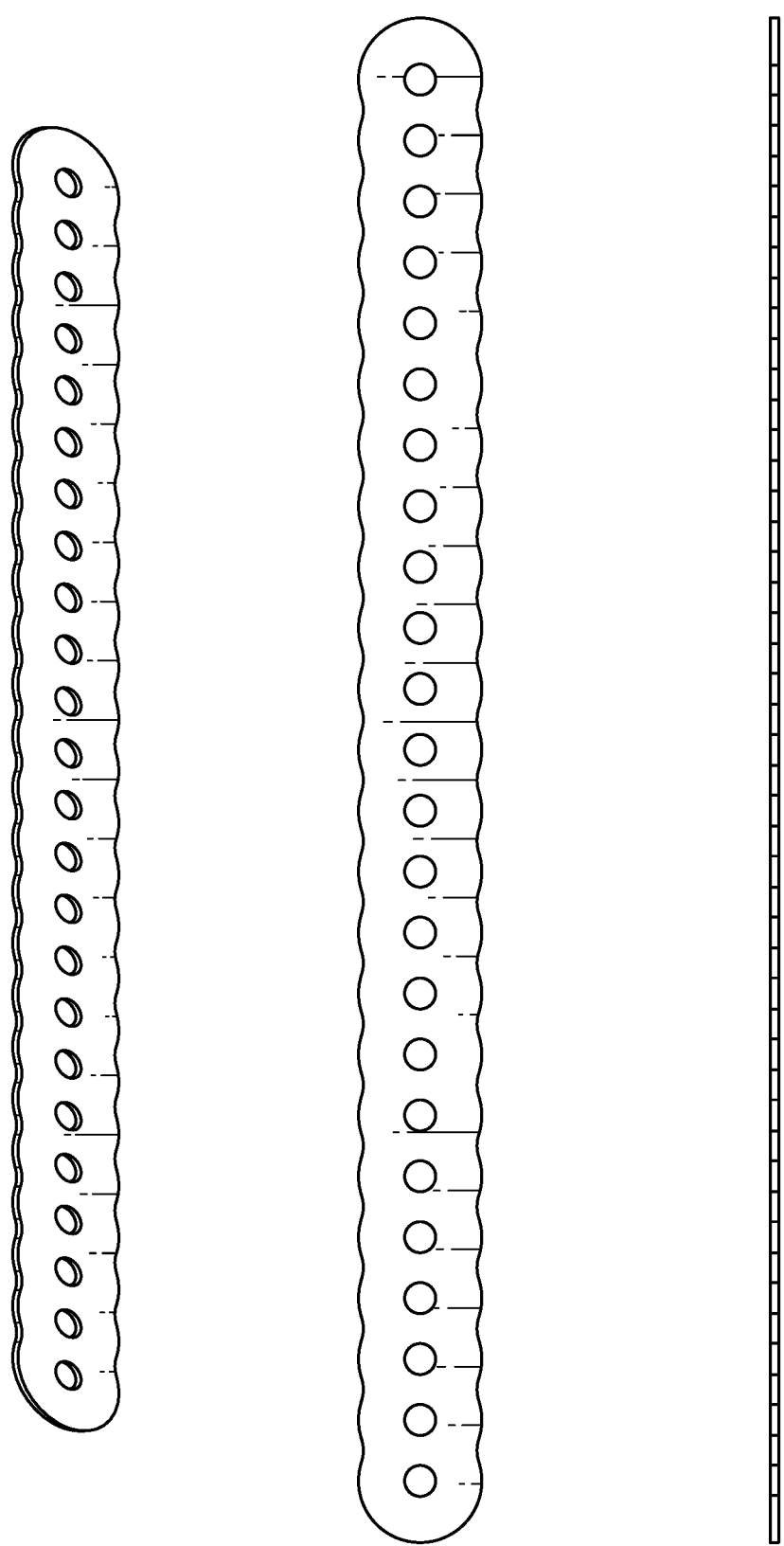
FIGS. 4A-C depict detailed views of a retention band of an embodiment.
Figure 5A:
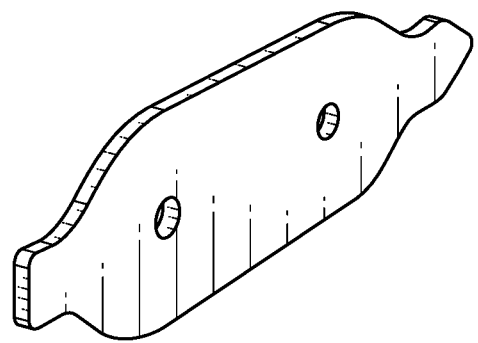
FIGS. 5A-D depict detailed views of an adapter of an embodiment.
Figure 5B:
Figure 5C:
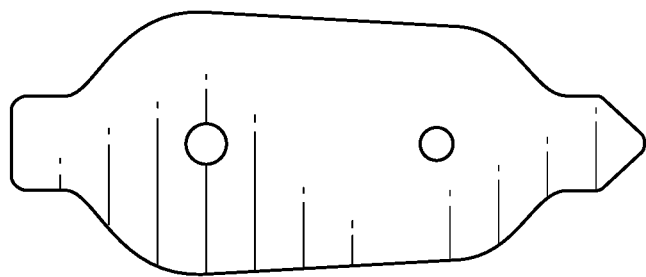
Figure 5D:
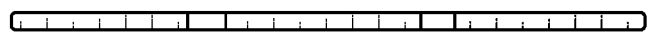
Figure 6A:
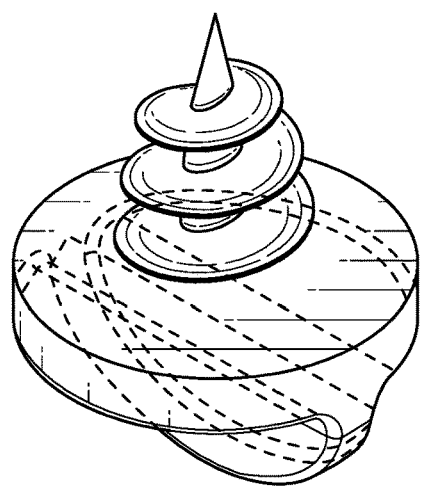
FIGS. 6A-E depict detailed views of a self-tapping thumbscrew of an embodiment.
Figure 6B:
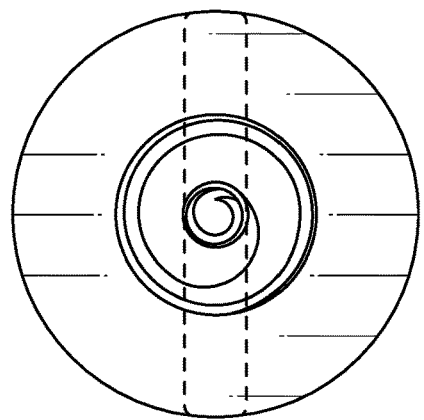
Figure 6C:
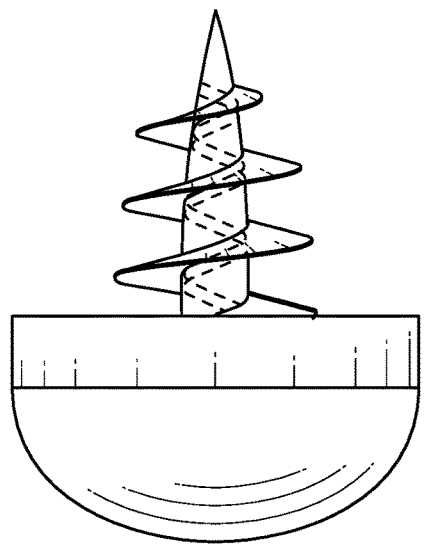
Figure 6D:
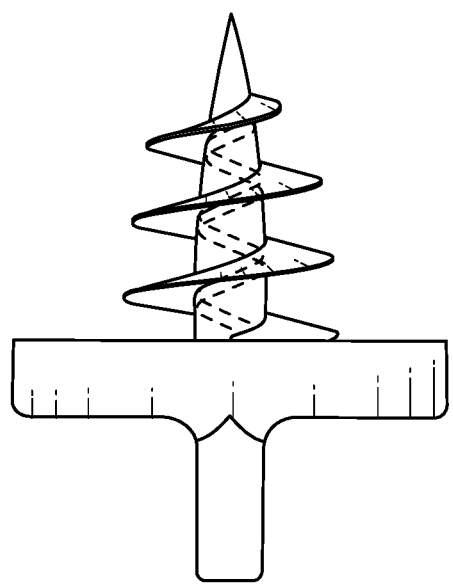
Figure 6E:
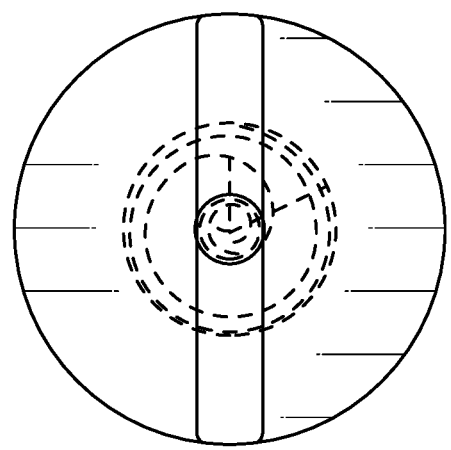
Figure 7C:
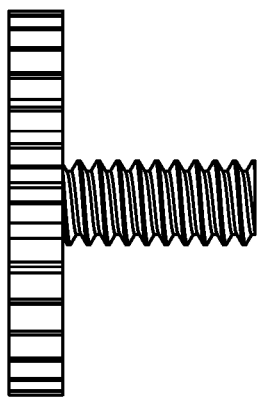
FIGS. 7A-E depict detailed views of a thumbscrew of an embodiment.
Figure 7E:
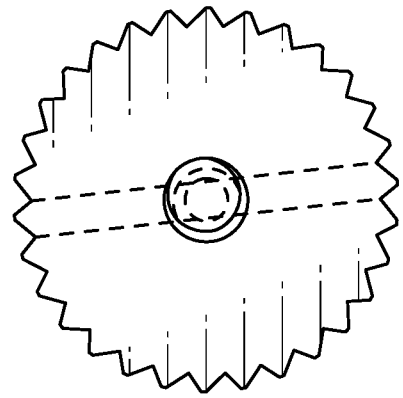
Figure 7B:
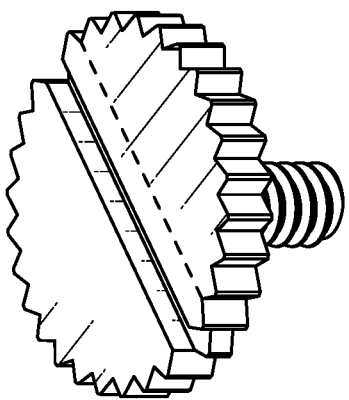
Figure 7D:
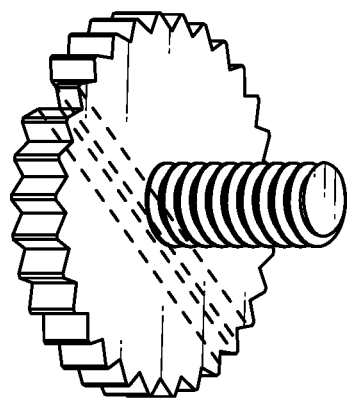
Figure 7A:
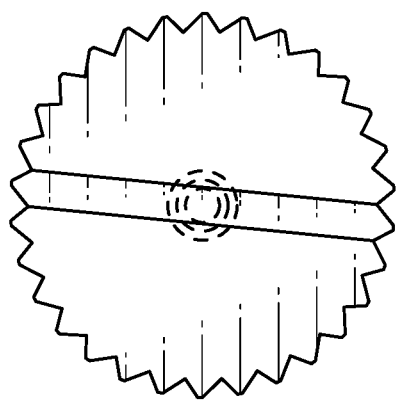
Figure 8B:
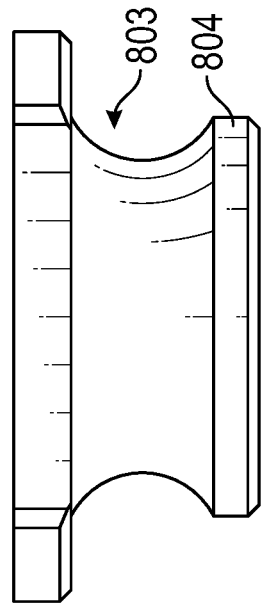
FIGS. 8A-G depict detailed views of a mounting bracket of an embodiment.
Figure 8D:
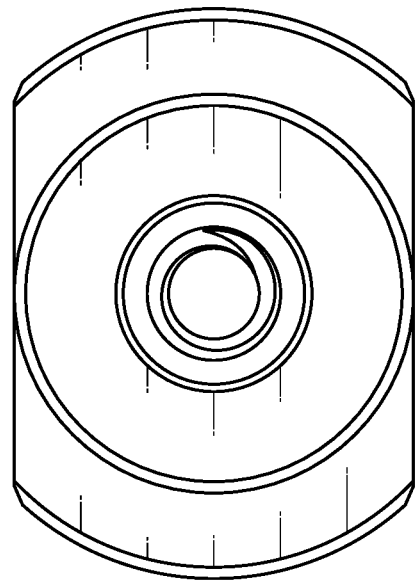
Figure 8A:
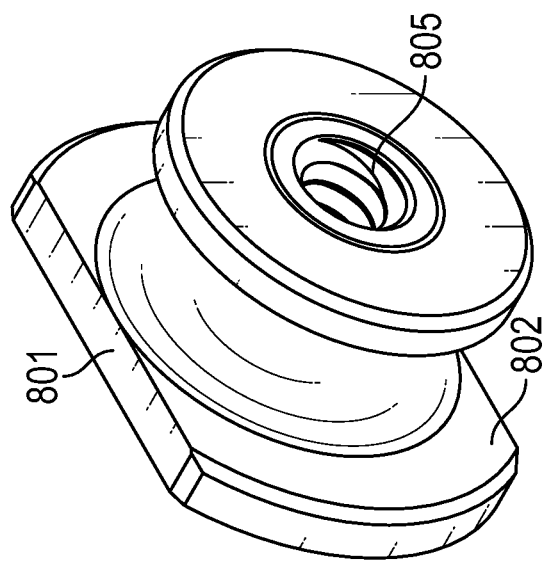
Figure 8C:
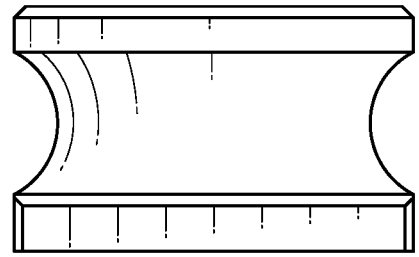
Figure 8F:
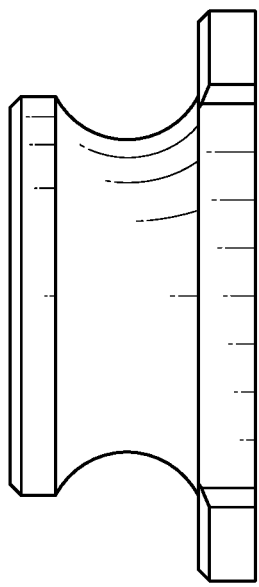
Figure 8G:
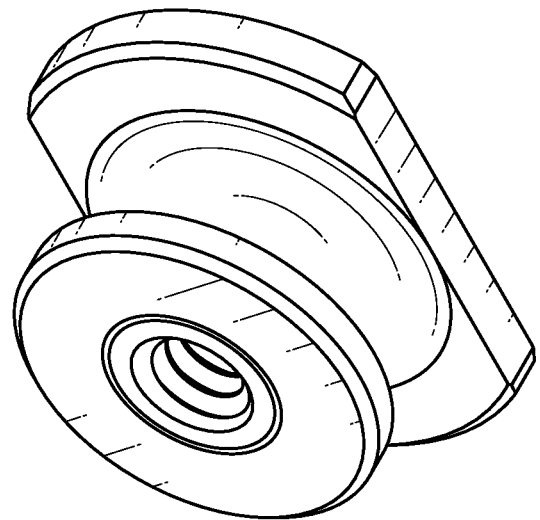
Figure 8E:
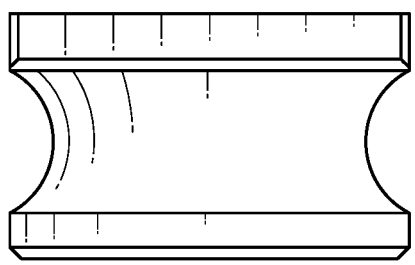

FIGS. 4A-C depict detailed views of a retention band of an embodiment. The band may be varied in length but generally will have enough adjustment openings to accommodate varying geometries of eyewear and will be elastic enough to permit securement of two of the adjustment openings to the mounting bracket.

FIGS. 5A-D depict detailed views of an adapter of an embodiment. The adapter may be constructed from various materials but preferably will be flexible to facilitate the user adjusting ear devices to their desired position. In the first embodiment, the adapter has two openings, one for securement to the mounting arm and one to an ear device.

FIGS. 6A-E depict detailed views of a self-tapping thumbscrew of an embodiment. This thumbscrew may be employed to secure various ear devices that may be easily threaded, particularly including common soft hearing protection ear buds.

FIGS. 7A-E depict detailed views of a thumbscrew of an embodiment. The thumbscrew may have a flat head face having a diameter greater than the width of the slot profile of a mounting arm to retain the mounting arm relative to the mounting bracket.

FIGS. 8A-G depict detailed views of a mounting bracket of an embodiment. The mounting bracket may include a flat upper surface 801 and lower surface 802 to profile against the temple of eyewear, while being elongated relative to the lengthwise direction of the temple. In such a configuration the retention band may wrap around the temple of the eyewear and securely hold the mounting bracket against the eyewear. The mounting bracket includes a circumferential indentation 803 in which the adjustment openings of the retention band may be secured. The mounting profile may include a retention section 804 that protrudes with a wider diameter than the circumferential indentation 803, which aids in retaining the retention band. The mounting bracket also includes a threaded orifice 805 for securement of a thumbscrew.

Figure 9A:
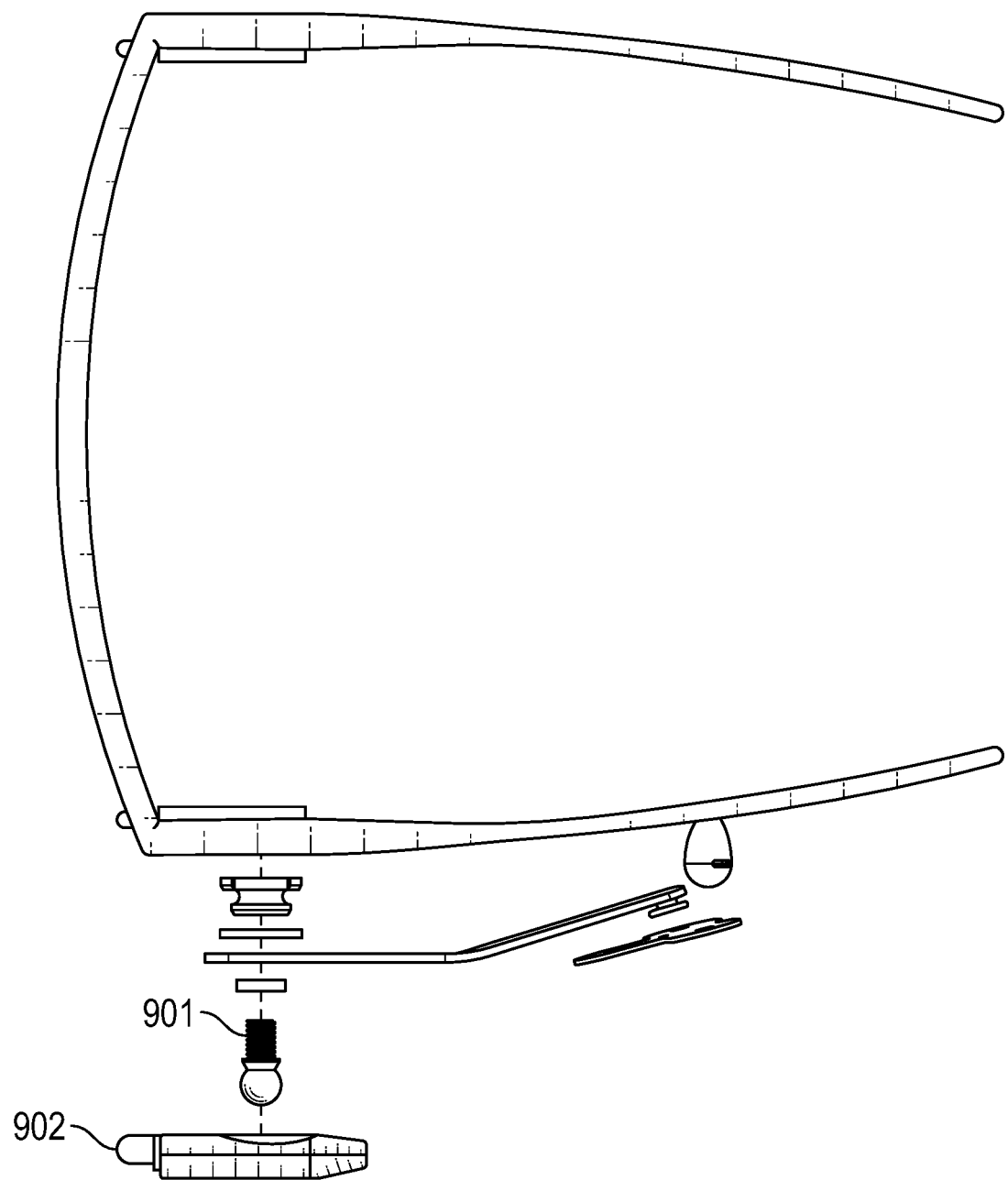
FIGS. 9A-C depict a second embodiment having a spherical rod end for securement of an illumination device and a second adapter for securement of an electronic hearing device such as an ear bud earphone.
Figure 9B:
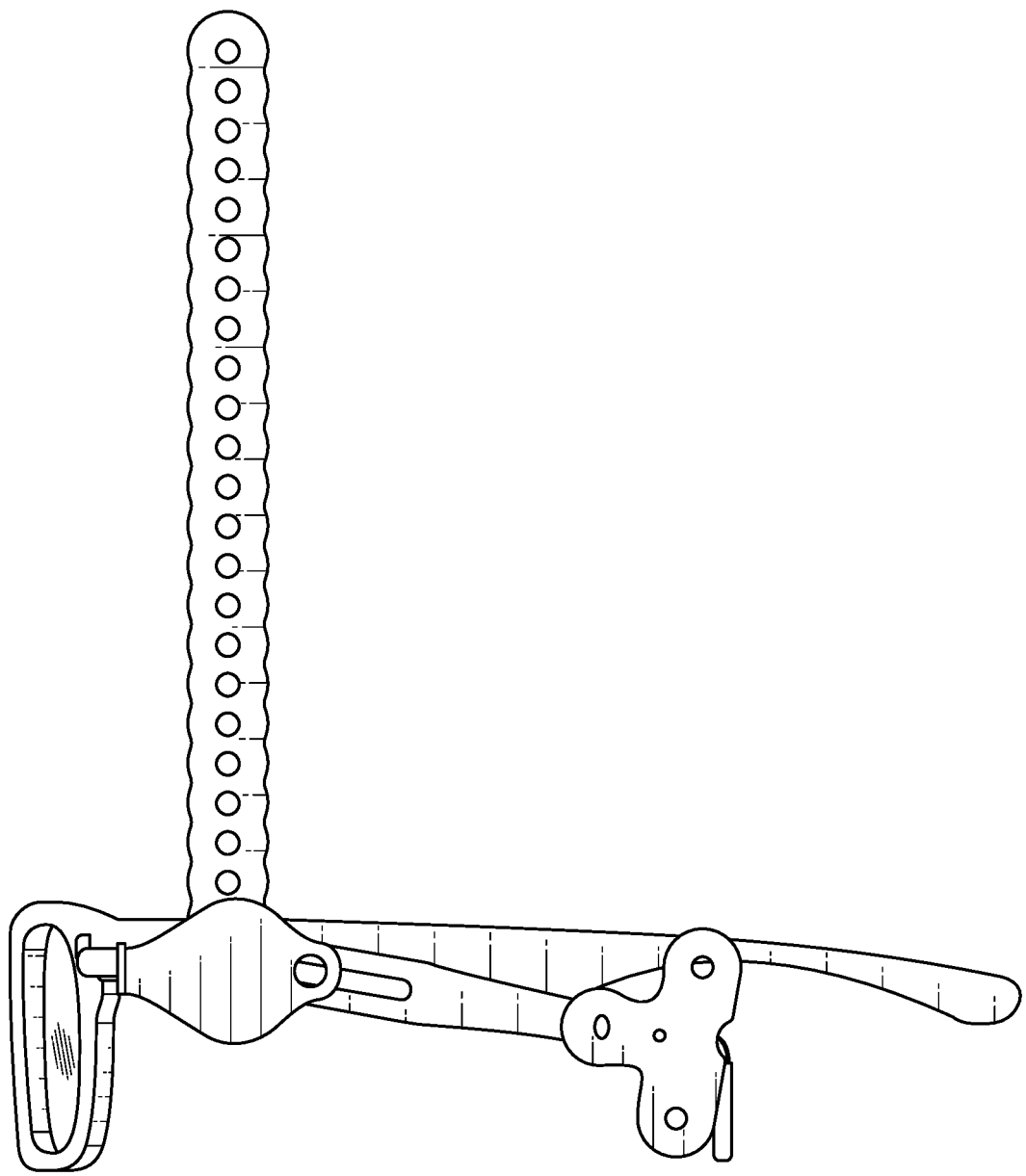
Figure 9C:
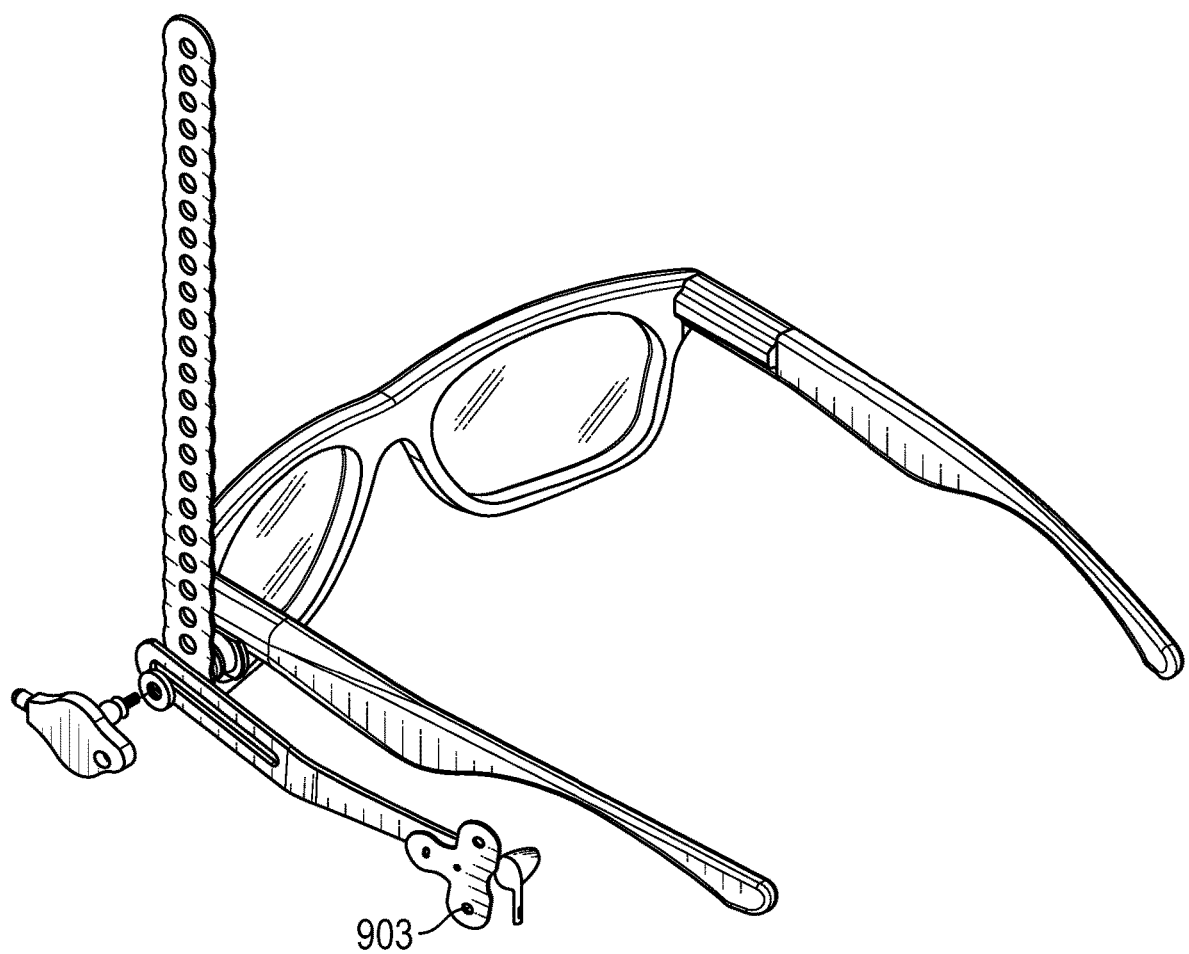
Figure 10A:
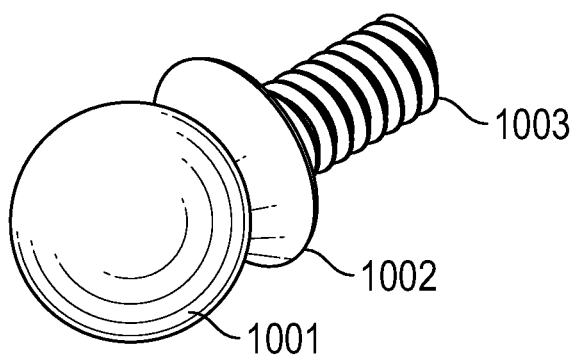
FIGS. 10A-E depict detailed views of the spherical rod end of the second embodiment.
Figure 10B:
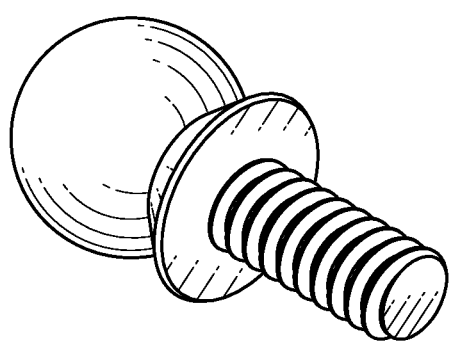
Figure 10C:
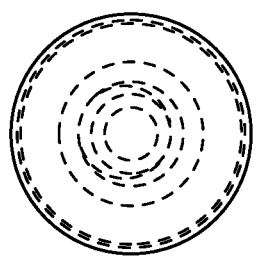
Figure 10D:
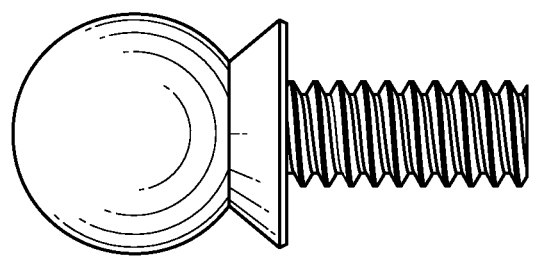
Figure 10E:
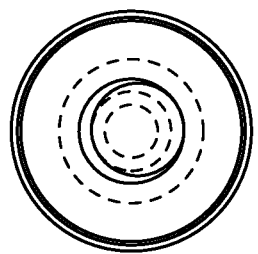

FIGS. 9A-C depict a second embodiment having a spherical rod end 901 for securement of an illumination device 902 and a second adapter 903 for securement of an electronic hearing device such as an ear bud earphone.

FIGS. 10A-E depict detailed views of the spherical rod end of the second embodiment. A spherical head 1001 is configured for interconnection with a socket on an illumination device. A retention section 1002 is configured to secure a mounting arm against a mounting bracket. A threaded section 1003 is configured for securement to a threaded orifice in the mounting bracket.

FIGS. 11A-C depict detailed views of the second adapter of the second embodiment. The adapter includes a first opening 1101 configured for securement to a protruding tab on a mounting arm. A second opening 1102 and third opening 1103 are configured to be folded over so as to be aligned, which allows insertion of the stem of an earbud hearing device.

Figure 12A:
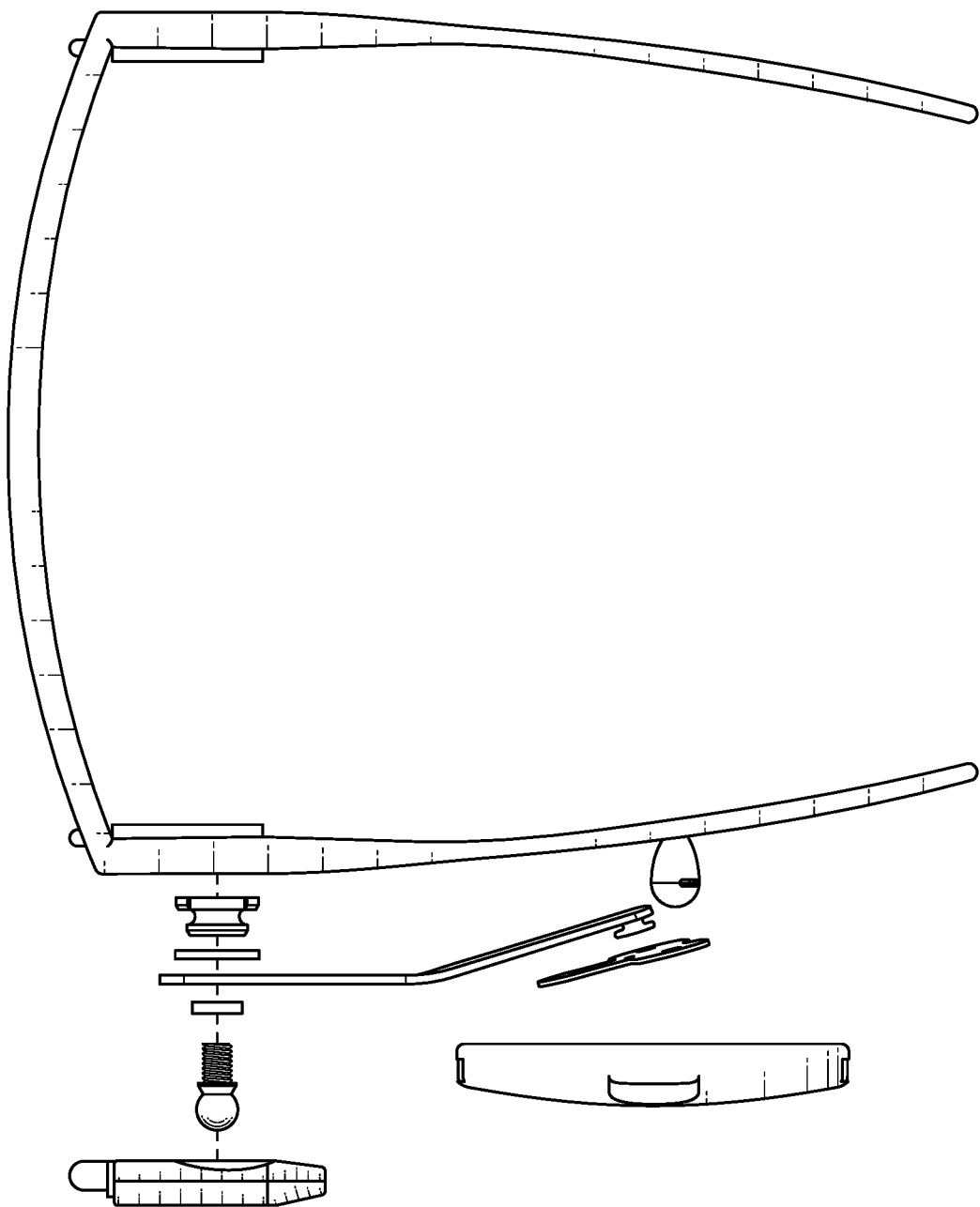
FIGS. 12A-C depict a third embodiment having an additional ear covering that does not interfere with the underlying ear bud headphones.
Figure 12B:
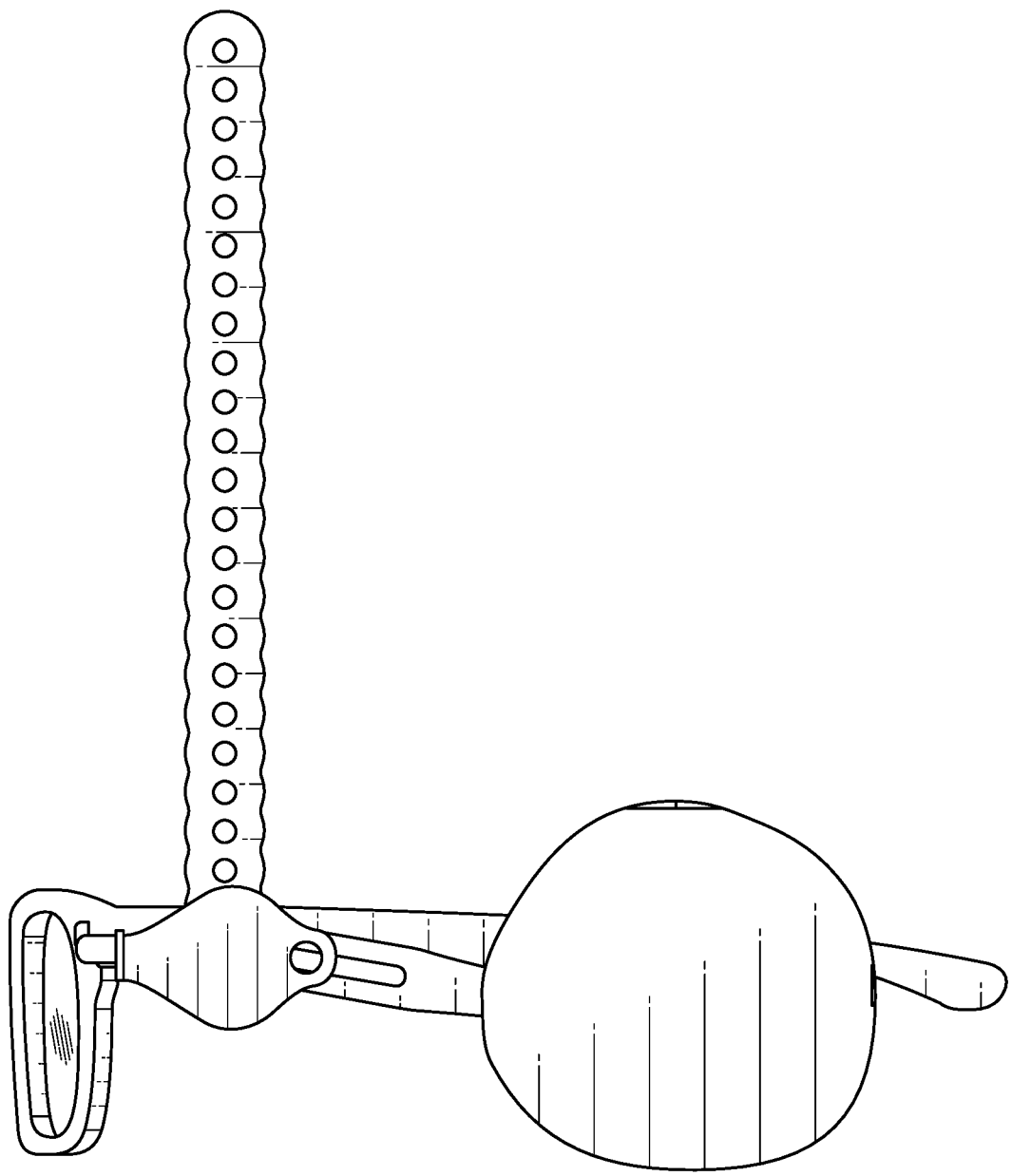
Figure 12C:
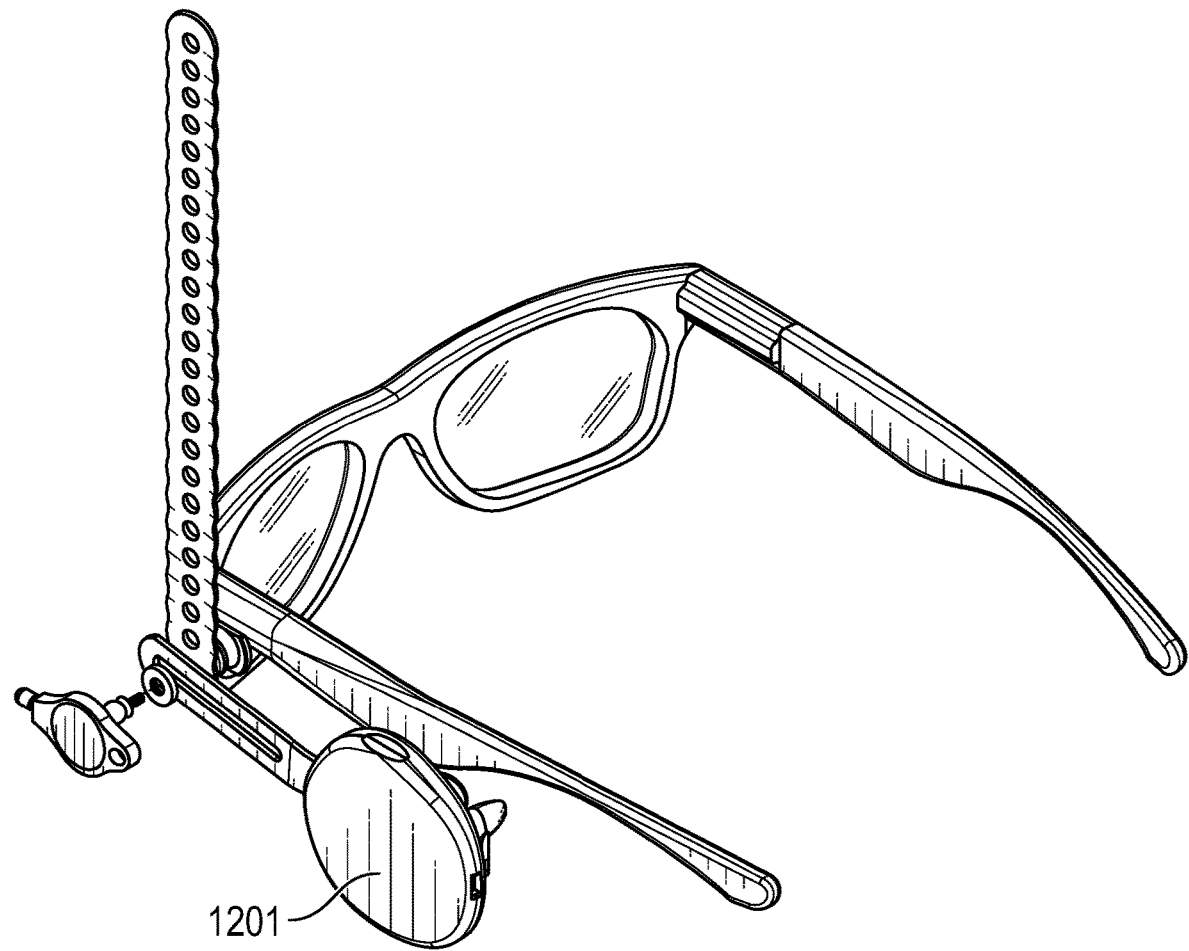
Figure 13A:
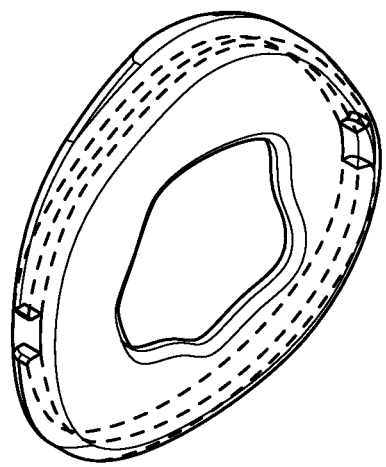
FIGS. 13A-F depict detailed views of the ear covering of the third embodiment.
Figure 13B:
Figure 13C:
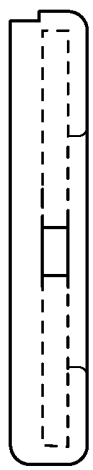
Figure 13D:
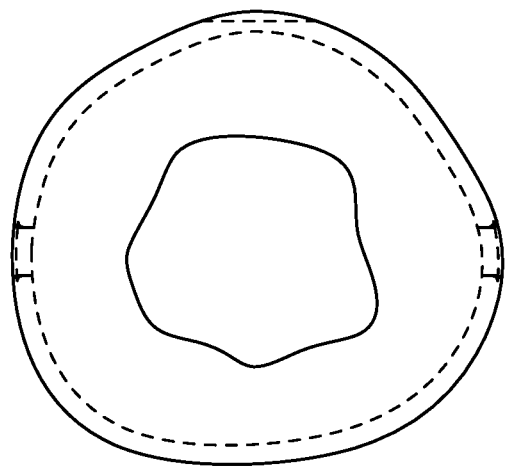
Figure 13E:
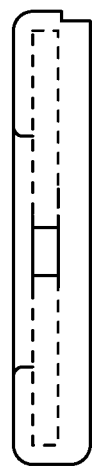
Figure 13F:
Figure 14C:
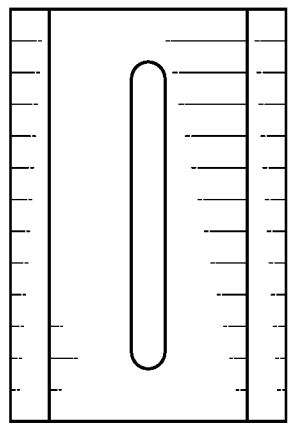
FIGS. 14A-E depict a bracket for connection to hearing protection devices.
Figure 14E:
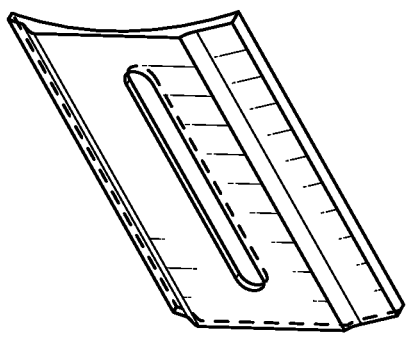
Figure 14B:
Figure 14D:
Figure 14A:
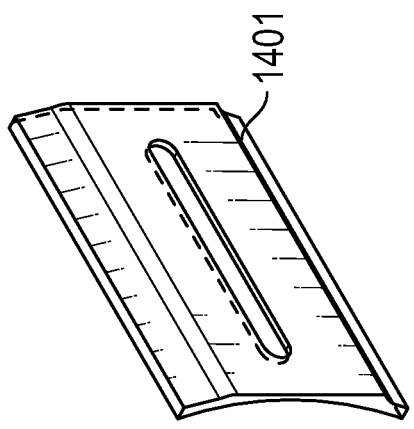

FIGS. 12A-C depict a third embodiment having an additional ear covering 1201 that does not interfere with the underlying ear bud headphones.

FIGS. 13A-F depict detailed views of the ear covering 1201 of the third embodiment.

FIGS. 14A-E depict a bracket 1401 for connection to hearing protection devices.

What is claimed:
1. A hardware mounting system for eyewear, comprising:
a mounting bracket including a mounting section, a retention section and a central section disposed between the mounting section and the retention section and including a circumferential indentation;

wherein the mounting section of the mounting bracket is configured to be disposed against a temple of an eyewear;

a retention band having a plurality of adjustment openings and configured to be wrapped around the temple of the eyewear, whereby a first adjustment opening and a second adjustment opening are aligned and secured to the retention section of the mounting bracket by the circumferential indentation;

a mounting arm secured to the retention section of the mounting bracket at a slot profile;

an adapter secured to the mounting arm; and a spherical rod end secured to the mounting bracket, a socket of an illumination device being secured to the spherical rod end.

2. The system of claim 1, wherein an opening of the adapter is secured to a protruding tab of the mounting arm.

3. The system of claim 2 wherein an ear device is secured to the adapter at a mounting point.

4. The system of claim 3 wherein the ear device is secured by a portion of the adapter being wrapped around an ear device.

5. The system of claim 3 wherein the ear device is a soft hearing protection device secured to the mounting point of the adapter via a threaded thumbscrew.

6. A method of attaching a hardware mounting system to eyewear, comprising the steps of:

disposing a mounting section of a mounting bracket against a temple of an eyewear, the mounting bracket further having a retention section and a central section including a circumferential indentation;

wrapping a retention band having a plurality of adjustment openings around the temple of the eyewear, whereby a first adjustment opening and a second adjustment opening are secured by the retention section of the mounting bracket in the circumferential indentation;

disposing a slot profile of a mounting arm against the retention section of the mounting bracket;

securing the mounting arm to the mounting bracket securing an adapter to the mounting arm;

securing a spherical rod end to the mounting bracket; and securing a socket of an illumination device to the spherical rod end.

7. The method of claim 6, wherein the adapter includes a plurality of openings and the step of securing the adapter to the mounting arm includes securing an opening of the adapter over a protruding tab.

8. The method of claim 7 further comprising the step of securing an ear device to the adapter at a mounting point.

9. The method of claim 8 wherein the step of securing the ear device includes threading a thumbscrew through the mounting point and into the ear device which is a soft hearing protection.

10. The method of claim 9 wherein the hearing protection device is a soft hearing protection device.

* * * * *